United States Patent
Tanaka et al.

(10) Patent No.: US 8,518,924 B2
(45) Date of Patent: *Aug. 27, 2013

(54) AGENT FOR INHIBITING VISCERAL FAT ACCUMULATION

(75) Inventors: Miyuki Tanaka, Zama (JP); Eriko Misawa, Zama (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 394 days.

This patent is subject to a terminal disclaimer.

(21) Appl. No.: 12/841,076

(22) Filed: Jul. 21, 2010

(65) Prior Publication Data

US 2010/0286104 A1 Nov. 11, 2010

Related U.S. Application Data

(63) Continuation of application No. 11/913,758, filed as application No. PCT/JP2006/318686 on Sep. 21, 2006, now Pat. No. 8,093,233.

(30) Foreign Application Priority Data

Sep. 22, 2005 (JP) ................................ 2005-275172
Sep. 30, 2005 (JP) ................................ 2005-287888

(51) Int. Cl.
*A61K 31/56* (2006.01)

(52) U.S. Cl.
USPC ......................................... 514/182; 514/177

(58) Field of Classification Search
USPC .............................................. 514/182
See application file for complete search history.

(56) References Cited

U.S. PATENT DOCUMENTS

| | | | |
|---|---|---|---|
| 4,851,224 A * | 7/1989 | McAnalley | 424/744 |
| 5,494,907 A | 2/1996 | Nique et al. | |
| 6,280,751 B1 | 8/2001 | Fletcher et al. | |
| 6,506,387 B1 | 1/2003 | Cohen | |
| 6,828,451 B2 | 12/2004 | Barrault et al. | |
| 2004/0156920 A1 * | 8/2004 | Kane | 424/725 |
| 2007/0032463 A1 | 2/2007 | Higuchi et al. | |

FOREIGN PATENT DOCUMENTS

| | | |
|---|---|---|
| CN | 1 426 702 A | 7/2003 |
| EP | 1731158 A1 * | 12/2006 |
| JP | 05-170651 | 7/1993 |
| JP | 07-165587 | 6/1995 |
| JP | 10-036283 | 2/1998 |
| JP | 11-193296 | 7/1999 |
| JP | 2000-319190 | 11/2000 |
| JP | 2001-240544 | 9/2001 |
| JP | 2003-286185 | 10/2003 |
| JP | 2005-015425 | 1/2005 |
| NZ | 330439 | 12/2000 |
| RU | 2 140 423 | 10/1999 |
| RU | 2 192 876 | 11/2002 |
| WO | WO 2004/105770 | 12/2004 |
| WO | WO 2005/094838 | 10/2005 |

OTHER PUBLICATIONS

First Examination Report dated Nov. 22, 2010 and issued to corresponding Indian patent application 4913/CHENP/2007 (English translation).
Mohammad Kabiruddin; Bayaaz-e-Kabir, vol. II (compiled), Daftar-al-Maseeh, Karol Bagh, New Delhi, 1938, p. 36.
Dundukanatha; Rasendracintamanaih Trans. Siddhinandan Mishra, Chaukhamba Orientalia (Varanasi) Ed. $1^{st}$ 1999, p. 348.
Rasatantrasarah Evam Siddhaprayogasamgrahah; Part I: Krishan Gopal Ayurveda Bhawan; Edn. $8^{th}$; 1990, pp. 266-267 (This book contains back references from 1000 BC to $20^{th}$ century).
Rasayoga Sagara-Compiled and translated by Vaidya Pandita Hariprapanna Ji, vol. II: Krishnadas Academy, Varanasi, Edn. Reprint, 1998, p. 561 (This book contains back references from 1000 BC to $20^{th}$ century).
Rasayoga Sagara-Compiled and translated by Vaidya Pandita Hariprapanna Ji, vol. II: Krishnadas Academy, Varanasi, Edn. Reprint, 1998, p. 213 (This book contains back references from 1000 BC to $20^{th}$ century).
Nityanathasiddhah; Rasaratnakarah-Rasendra Khandam Comm. Datto Vallal Borakara, Ed. $2^{nd}$, 1986, Shri Gajanau Book Depot (Pune), pp. 387-389.
Cudamani; Rasakamadhenu Samhita-Edited by Jiraramakalidasa Sastri, Part 4, Chaukhambha Publishers, Varanasi, Edn. $1^{st}$, 1992, p. 382.
Communication from European Patent Office issued to application No. 06798178.7-1216/1927360, dated Jul. 26, 2010 with Annexes 1-3.
Panosyan, et al. "Sterols and Sterol Glycosides of *Bryonia alba*," *Khimiya Prirodnykh Soedinenii*, vol. 3, pp. 353-360, 1977 with English abstract.
Decision of Grant dated Nov. 29, 2010 and issued to related Russian patent application No. 2007146364/15(050817).
Itoh, et al. "Four New and Other 4α-Methylsterols in the Seeds of Solanaceae," *Phytochemistry*, vol. 17, No. 5, pp. 971-977, 1978.
Tanaka, et al. "Identification of Five Phytosterols from Aloe Vera Gel as Anti-Diabetic Compounds," *Biol. Pharm. Bull.*, vol. 29, No. 7, pp. 1418-1422, 2006.
Igaku to Seibutsugaku, vol. 125, No. 5, pp. 189-194, Nov. 10, 1992.
Journal of Medicine of Fujita Gakuen, vol. 22, No. 2, pp. 153-157, 1998.
Database WPI Week 200116, AN 2001-151412, JP 2000-319190, Nippon Menard Keshohin KK, Nov. 21, 2000, abstract.
Database WPI Week 200363, AN 2003-664236, CN 1426702 You, Jul. 2, 2003, abstract.
Chan, et al. "Mechanism of Action of a 3-Hydroxy-3-Methylglutaryl Coenzyme a Reductase Inhibitor on Apolipoprotein B-100 Kinetics in Visceral Obesity," *The Journal of Clinical Endocrinology & Metabolism*, vol. 87, No. 5, pp. 2283-2289, 2002.
Miettinen, et al. "Cholesterol Absorption Efficiency and Sterol Metabolism in Obesity," *Atherosclerosis*, vol. 153, pp. 241-248, 2000.

(Continued)

*Primary Examiner* — Melenie McCormick
*Assistant Examiner* — Timothy Betton
(74) *Attorney, Agent, or Firm* — Knobbe, Martens, Olson & Bear LLP

(57) ABSTRACT

To reduce amounts of fat accumulated in abdominal cavity and to prevent or ameliorate visceral fat type obesity, considered to be a main factor of metabolic syndrome, the present invention provides an agent or a food or drink which contains a compound having a lophenol skeleton, or an organic solvent extract or a hot water extract of a Liliaceae plant, or a fraction thereof containing the compound as an active ingredient.

3 Claims, No Drawings

(56) References Cited

OTHER PUBLICATIONS

Riches, et al. "Reduction in Visceral Adipose Tissue is Associated with Improvement in Apolipoprotein B-100 Metabolism in Obese Men," *The Journal of Clinical Endocrinology and Metabolism*, vol. 84, No. 8, pp. 2854-2861, 1999.

Supplementary European Search Report dated Aug. 31, 2010, issued to European patent application EP 06 79 8178.

Ehrich, et al. "Diet, Obesity, and Hyperglycemia in LG/J and SM/J Mice," *Obesity Research*, vol. 11, pp. 1400-1410, 2003 (14 pages as downloaded from http://www.nature.com/oby/journal/v11/n11/full/oby2003189a.html.

\* cited by examiner

AGENT FOR INHIBITING VISCERAL FAT ACCUMULATION

RELATED APPLICATIONS

This application is a continuation of U.S. application Ser. No. 11/913,758, filed Nov. 6, 2007, which is incorporated herein by reference and which is the U.S. National Phase under 35 U.S.C. §371 of International Application PCT/JP2006/318686, filed Sep. 21, 2006, which was published in a non-English language, which claims priority to JP Application No. 2005-275172, filed Sep. 22, 2005 and JP Application No. 2005-287888, filed Sep. 30, 2005.

TECHNICAL FIELD

The present invention relates to an agent for inhibiting visceral fat accumulation, which contains a compound having a lophenol skeleton as an active ingredient, and to food or drink containing the same. In particular, the present invention relates to an agent for inhibiting visceral fat accumulation, capable of reducing an amount of fat accumulated in abdominal cavity and preventing or ameliorating visceral fat type obesity which is considered to be a main factor of metabolic syndrome, and to a physiologically functional food or drink, such as food for specified health uses, containing the agent for inhibiting visceral fat accumulation.

BACKGROUND ART

In recent years, a rapid increase in obesity involved in westernization of lifestyle has become a serious problem. The obesity means a state in which excessive energy is accumulated owing to excessive ingestion of calorie and a decrease in calorie consumption caused by insufficient exercise or the like, and refers to "state where excessive amount of fat tissues of body (body fat) is accumulated". The obesity is indicated as a basis of onset of so-called lifestyle-related diseases such as diabetes, hypertension, and hyperlipidemia and so forth.

The obesity exhibits a state of accumulation of excessive body fat and a phenomenon of a body weight increase. It is reported that, when rapid reduction of a body weight is conducted to ameliorate obesity, amounts of muscles playing a role in energy consumption also reduce together with the fat, and in a case of elders, symptoms such as blood pressure disorder and injury of articulatio coxae may occur (Non-patent Document 1). In addition, for a case where reduction of the amount of fat is conducted without reducing a body weight, there is a report on exercise therapy which is expected to exert an effect of improving muscle tissues (Non-patent Document 2). As described above, in recent years, there have been made attention on methods of ameliorating obesity by inhibiting accumulation of body fat, not by reducing a body weight.

The fat tissues are grouped into subcutaneous fat which is accumulated inside of a skin and visceral fat which is accumulated around visceral organs in an abdominal cavity, which are collectively called "body fat". It is known that obesity is classified into two types, subcutaneous fat type obesity involving accumulation of the subcutaneous fat and visceral fat type obesity involving accumulation of the visceral fat. The visceral fat accumulation particularly gives large effects on frequency of onset of complications such as abnormal metabolism and cardiovascular diseases in obesity and severity thereof.

Conventionally, it has been known that pathosis in which an individual is suffering from a combination of a plurality of lifestyle-related diseases, that is, "multiple risk factor syndrome", significantly increases the risks of onset of arteriosclerotic disease, and concepts such as Syndrome X and metabolic syndrome have been proposed as risk factors of arteriosclerotic disease. In order to evaluate comprehensive risk and prevent of the onset of arteriosclerotic disease in those multiple risk factor syndromes, international integration of definition of metabolic syndrome and diagnostic criteria therefore were conducted (Non-patent Document 3). In the diagnostic criteria for metabolic syndrome which was proposed in Japan in April 2005, a waist size corresponding to a visceral fat area of 100 $cm^2$ or more is adopted as an essential item instead of a body mass index (BMI) or a body fat percentage which is generally used for indicating a level of obesity. Thus, the visceral fat accumulation has been recognized to be largely involved in the cause of metabolic syndrome.

Exercise, diet, and behavior therapies are recommended as measures for reducing body fat. However, in a case where those therapies are difficult to be carried out or continued, drug therapy or a surgery may be conducted. At present, mazindol that is an anorectic is used as a therapeutic drug for obesity, and is prescribed basically for people suffering from high levels of obesity which show BMI of 35 or more. However, mazindol not only gives side effects such as headache and dry mouth, but has a large number of problems in that mazindol has contraindication when severe dysfunctions are present in the kidney, liver, or pancreas, and cannot be administered for a long period of time because of its dependency, and the like.

Plant sterols such as β-sitosterol, campesterol, stigmasterol have been known to have a reducing effect on blood cholesterol by inhibiting absorption of the cholesterol, and there is disclosed a lipid metabolism-improving agent containing diglyceride and a plant sterol as active ingredients (Patent Document 1). Further, there are disclosed an anti-obesity agent and a lipid metabolism-improving agent containing, as an active ingredient, a cholestenone compound which is synthesized by using as a starting material the plant sterols such as β-sitosterol and campesterol, or 4-cholesten-3-one (Patent Documents 2 to 5).

As typical plants belonging to the genus *Aloe* of the family Liliaceae, *Aloe* vera (*Aloe barbadenisis* Miller) and *Aloe arborescen* (*Aloe arborescen* Miller var. *natalensis* Berger) have been known, and various effects of these plants have been reported. Specifically, it is disclosed that an *Aloe* extract has a preventive or ameliorating effect on obesity (Patent Document 6). In addition, there are disclosed a supplement having an effect of reducing a body weight, which contains 0.25% *Aloe* vera powder (Patent Document 7) and an essential oil composition for controlling a body weight, which contains *Aloe* vera (Patent Document 8), respectively. Further, it is reported that administration of a whole leaf of *Aloe arborescens* to a rat resulted in a significant decrease in a body weight depending on concentrations of *Aloe arborescens* (Non-patent Document 4 or 5).

[Patent Document 1] Japanese patent Laid-open NO. 2005-15425

[Patent Document 2] Japanese patent Laid-open NO. 07-165587

[Patent Document 3] Japanese patent Laid-open NO. 11-193296

[Patent Document 4] Japanese patent Laid-open NO. 2001-240544

[Patent Document 5] Japanese patent Laid-open NO. 05-170651

[Patent Document 6] Japanese patent Laid-open NO. 2000-319190

[Patent Document 7] New Zealand Patent No. 330439

[Patent Document 8] U.S. Pat. No. 6,280,751

[Non-patent Document 1] Journal of Applied Physiology, vol. 95, p. 1728-1736, 2003

[Non-patent Document 2] Journal of Applied Physiology, vol. 99, p. 1220-1225, 2005

[Non-patent Document 3] Adiposcience, vol. 2, p. 11-15, 2005

[Non-patent Document 4] Medical and Biology, 125(5), p. 189-194

[Non-patent Document 5] Bulletin of the Fujita Medical Society, 22(2), p. 153-157

DISCLOSURE OF THE INVENTION

Patent Document 1 does not describe an effect of administration of plant sterol alone, and does not describe or suggest at all the effect of the plant sterol on visceral fat.

In addition, there are disclosed that the 3-ketosteroid compound disclosed in Patent Document 2, the cholestenone compound disclosed in Patent Document 3, and 24-alkyl-cholesten-3-one compounds such as 24-methylcholest-5-en-3-one disclosed in Patent Document 4 have effects of reducing a body weight, an amount of body fat, and an amount of blood lipid. However, there is no description or suggestion that the compounds have an effect of inhibiting visceral fat accumulation without affecting an amount of oral ingestion and an increase in body weight.

4-cholesten-3-one disclosed in Patent Document 5 is apparently different from the active ingredient of the present invention. Specifically, the effect of 4-cholesten-3-one described in Patent Document 5 is that, when a normal mouse ingests calories, the compound reduces, beyond necessity, fat components regarded to be within a normal range together with an excessive amount of fat in an abdominal cavity. Therefore, the effect of 4-cholesten-3-one is clearly different from the effect of the present invention, that is, an effect of effectively inhibiting only the fat components accumulated around visceral organs in an amount more than that required in a case of an obese state or in a case where excessive amounts of calories are ingested.

Further, there is disclosed that the agent for preventing and ameliorating obesity of Patent Document 6 inhibits progression of obesity involving an increase in body weight, and thus is effective for maintaining a standard body weight without a need for excessive diet restriction. However, there is no description on the effect on the body fat, and no description about the effect of inhibiting visceral fat accumulation, which reduces the amount of visceral fat without reducing a body weight.

In addition, the active ingredient described in Patent Document 6 is an Aloe extract. However, components related to the inhibition of the progression of obesity involving an increase in body weight are not specified at all. Therefore, it is difficult to predict presence of the effect of inhibiting visceral fat accumulation, which reduces only the visceral fat without reducing a body weight, that is an effect which cannot be anticipated from the description in Patent Document 6.

Accordingly, with regard to an agent capable of selectively reducing the visceral fat which is strongly related to onset of metabolic syndrome, or capable of preventing and inhibiting accumulation thereof, there has been demanded a further development of a functional material which can be ingested daily safely with pain as little as possible, and can efficiently reduce the visceral fat.

In view of the aforementioned circumstances, the inventors of the present invention have made extensive studies on an agent for inhibiting visceral fat accumulation, which can prevent or ameliorate visceral fat type obesity that is considered to be a main cause of metabolic syndrome. As a result, the inventors of the present invention have found that a compound having a lophenol skeleton has an effect of efficiently reducing fat accumulated in an abdominal cavity. In addition, it was found that the compound has an effect of maintaining a standard body weight without reducing the body weight, and thus is useful for inhibiting progression of obesity without a need for excessive diet restriction.

An object of the present invention is to provide an agent for inhibiting visceral fat accumulation, which contains the compound having a lophenol skeleton as an active ingredient. In addition, it is another object of the present invention to provide a physiologically functional food or drink such as food for specified health uses containing the agent for inhibiting visceral fat accumulation.

First invention of the present application to solve the aforementioned problems is an agent for inhibiting visceral fat accumulation, containing a compound represented by the following general formula (1) as an active ingredient.

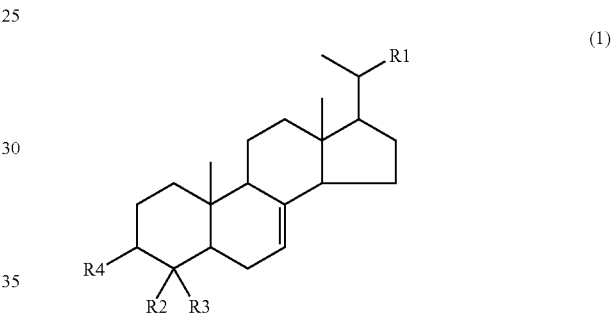

(1)

(In the formula, R1 represents an alkyl group, or an alkenyl group having 1 or 2 double bonds, or a substituted alkyl or alkenyl group having a hydroxyl group and/or a carbonyl group, which is straight or branched chain having 5 to carbon atoms, R2 and R3 each independently represent a hydrogen atom, an alkyl group or a substituted alkyl group having 1 to 3 carbon atoms, and R4 forms C=O with the carbon atom constituting the ring or represents —OH or —OCOCH$_3$.)

Further, the following 1) to 4) are preferred embodiments.

1) In the aforementioned compound, one of R2 and R3 is a hydrogen atom, the other is methyl group, and R4 is a hydroxyl group.

2) In the aforementioned 1), R1 is represented by any one of the following formulas:

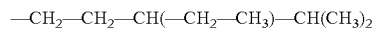

—CH$_2$—CH$_2$—CH(—CH$_2$—CH$_3$)—CH(CH$_3$)$_2$

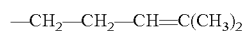

—CH$_2$—CH$_2$—CH=C(CH$_3$)$_2$

—CH$_2$—CH=C(CH$_3$)—CH(CH$_3$)$_2$

—CH$_2$—CH$_2$—C(=CH—CH$_3$)—CH(CH$_3$)$_2$

—CH$_2$—CH$_2$—CH(Ra)=C(CH$_3$)Rb (wherein Ra and Rb is any of —H, —OH, or —CH$_3$)

—CH$_2$—CH$_2$—CH(Rc)—CH(CH$_3$)Rd (wherein Rc and Rd is any of —H, —OH, or —CH$_3$)

3) The aforementioned compound described in 2) is selected from the group consisting of 4-methylcholest-7-en-3-ol, 4-methylergost-7-en-3-ol and 4-methylstigmast-7-en-3-ol.

4) The aforementioned compound described in 1) to 3) is contained in an amount of at least 0.001% by mass.

Second invention of the present application to solve the aforementioned problems is an agent for inhibiting visceral fat accumulation, containing an organic solvent extract or a hot water extract of a Liliaceae plant, or a fraction thereof, which contains a compound represented by the following general formula (1), and in which the organic solvent extract or the hot water extract of the aforementioned Liliaceae plant, or the fraction thereof contains as an active ingredient a composition containing at least 0.001% by dry mass of the compound represented by the following general formula (1).

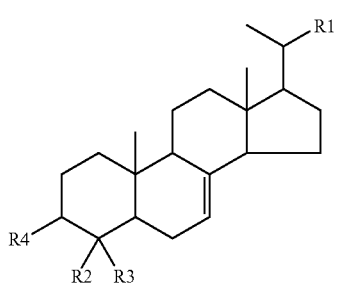

(1)

(In the formula, R1 represents an alkyl group, or an alkenyl group having 1 or 2 double bonds, or a substituted alkyl or alkenyl group having a hydroxyl group and/or a carbonyl group, which is straight or branched chain having 5 to 16 carbon atoms, R2 and R3 each independently represent a hydrogen atom, an alkyl group or a substituted alkyl group having 1 to 3 carbon atoms, and R4 forms C=O with the carbon atom constituting the ring or represents —OH or —OCOCH$_3$.)

Further, the following 5) to 7) are preferred embodiments.

5) In the aforementioned compound, one of R2 and R3 is a hydrogen atom, the other is methyl group, and R4 is a hydroxyl group.

6) In the aforementioned 5), R1 is represented by any one of the following formulas:

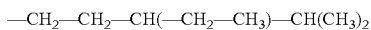

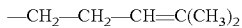

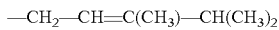

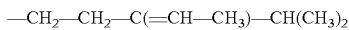

—CH$_2$—CH$_2$—CH(Ra)=C(CH$_3$)Rb (wherein Ra and Rb is any of —H, —OH, or —CH$_3$)

—CH$_2$—CH$_2$—CH(Rc)-CH(CH$_3$)Rd (wherein Rc and Rd is any of —H, —OH, or —CH$_3$)

7) The aforementioned compound described in 6) is selected from the group consisting of 4-methylcholest-7-en-3-ol, 4-methylergost-7-en-3-ol and 4-methylstigmast-7-en-3-ol.

Third invention of the present application to solve the aforementioned problems is a food or drink containing the aforementioned agent for inhibiting visceral fat accumulation according to the first or second invention.

In addition, the following 8) is a preferred embodiment.

8) The food or drink contains the compound represented by the aforementioned general formula (1) in an amount of 0.0001% by mass or more.

Fourth invention of the present application to solve the aforementioned problems is use of a compound represented by the aforementioned general formula (1), or an organic solvent extract or hot water extract of a Liliaceae plant, or a fraction thereof which contains at least 0.001% by dry mass of the compound for production of an agent for inhibiting visceral fat accumulation.

Fifth invention of the present application to solve the aforementioned problems is a method of inhibiting visceral fat accumulation, which comprises administering a compound represented by the aforementioned general formula (1), or an organic solvent extract or hot water extract of a Liliaceae plant, or a fraction thereof, which contains at least 0.001% by dry mass of the compound to a subject whose the visceral fat accumulation is to be inhibited.

In the aforementioned use and method of the present invention, preferred embodiments of the compound represented by the aforementioned general formula (1) are the same as that of the second invention of the present application.

The agent for inhibiting visceral fat accumulation of the present invention and the food or drink containing the same can be administered or ingested safely, and have an effect of effectively inhibiting the visceral fat accumulation. In addition, the active ingredient of the agent for inhibiting visceral fat accumulation of the present invention can be ingested safely from experience, and can easily be produced from available Liliaceae plants such as *Aloe* vera (*Aloe barbadensis* Miller).

BEST MODE FOR CARRYING OUT THE INVENTION

Next, preferred embodiments of the present invention are described in detail. However, the present invention is not limited to the following preferable embodiments, and modifications can be freely made within the scope of the present invention. Note that, percentage as used herein indicates percentage by mass unless otherwise specified.

In the present invention, the effect of inhibiting visceral fat accumulation means an effect of reducing an amount of fat accumulated in an abdominal cavity. Therefore, the effect of inhibiting visceral fat accumulation can be evaluated by measuring an amount of fat in an abdominal cavity, for example, a weight of mesenteric fat.

The compound used as the active ingredient of the agent for inhibiting visceral fat accumulation of the present invention (hereinafter, also referred to as "agent of the present invention") is the compound having the structure represented by the aforementioned general formula (1), and any derivatives and the like of the compound are included as the active ingredient so long as they each are a compound having the effect of inhibiting visceral fat accumulation (hereinafter, also referred to as "compound of the present invention").

It is most preferred that a purity of the compound of the present invention which is used as the active ingredient of the agent for inhibiting visceral fat accumulation of the present invention is 100%. However, the purity can be appropriately set within a range where the compound exerts the effect of inhibiting visceral fat accumulation.

In addition, the composition which is used as an active ingredient of the agent for inhibiting visceral fat accumulation of the present invention (hereinafter, also referred to as "composition of the present invention") is an extract of a Liliaceae plant or a fraction thereof, which contains the aforementioned compound in an amount of at least 0.001% by dry mass, preferably 0.01% by dry mass or more, and more preferably 0.1% by dry mass or more. The upper limit of the content of the compound of the present invention is, but not particularly limited to, and it may be preferably 10% by dry mass, 50% by dry mass, 70% by dry mass, or 90% by dry mass, for example.

"Dry mass" as used in the present invention means a mass measured after a compound is dried by the drying method defined by "Drying Loss Test" that is a general test method as described in Japanese Pharmacopoeia, 14th Revision, (Mar. 30, 2001, Japan Ministry of Health, Labor and Welfare, Ministerial Notification No. 111). For example, the mass of the compound of the present invention can be determined in such a manner that: about 1 g of the compound of the present invention is measured off, and dried at 105° C. for 4 hours; and the resultant is cooled by standing in a desiccator; and the mass of the compound is weighed with a scale.

In the aforementioned general formula (1), R1 represents an alkyl group or an alkenyl group having 1 or 2 double bonds, which is straight or branched chain having 5 to 16 carbon atoms. Note that the aforementioned alkyl group and alkenyl group may be a substituted alkyl and alkenyl group having a hydroxyl group and/or a carbonyl group, respectively. R2 and R3 each independently represent a hydrogen atom, an alkyl group or a substituted alkyl group having 1 to 3 carbon atoms, and R4 forms C=O with the carbon atom constituting the ring or represents —OH or —OCOCH$_3$. As the aforementioned alkyl group having 1 to 3 carbon atoms, methyl group, ethyl group and so forth are preferred, and methyl group is particularly preferred.

The aforementioned R1 is preferably any one of the groups represented by the following formulas.

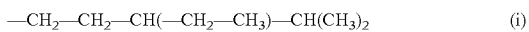

—CH$_2$—CH$_2$—CH(—CH$_2$—CH$_3$)—CH(CH$_3$)$_2$  (i)

—CH$_2$—CH$_2$—CH=C(CH$_3$)$_2$  (ii)

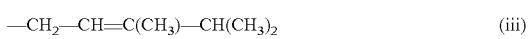

—CH$_2$—CH=C(CH$_3$)—CH(CH$_3$)$_2$  (iii)

—CH$_2$—CH$_2$—C(=CH—CH$_3$)—CH(CH$_3$)$_2$  (iv)

—CH$_2$—CH$_2$—CH(Ra)=C(CH$_3$)Rb  (v)

(wherein Ra and Rb is any of —H, —OH, or —CH$_3$)

—CH$_2$—CH$_2$—CH(Rc)-CH(CH$_3$)Rd  (vi)

(wherein Rc and Rd is any of —H, —OH, or —CH$_3$)

Further, it is preferred that one of R2 or R3 is a hydrogen atom, and the other is a methyl group. Further, it is preferred that R4 is a hydroxyl group.

The most preferred compounds as the aforementioned compound are those represented by the following formulas, 4-methylcholest-7-en-3-ol (formula (2)), 4-methylergost-7-en-3-ol (formula (3)) and 4-methylstigmast-7-en-3-ol (formula (4)).

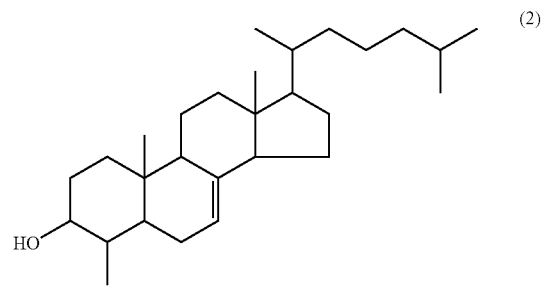

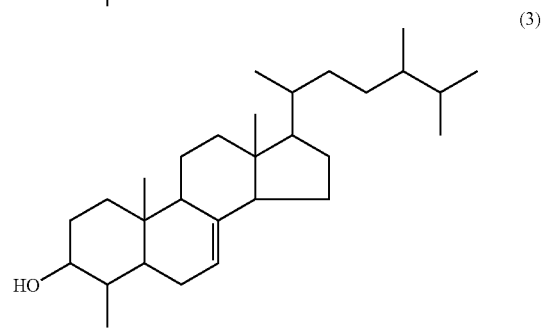

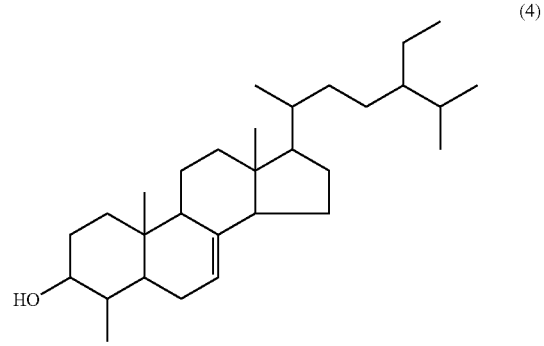

That is, 4-methylcholest-7-en-3-ol is a compound represented by the aforementioned general formula (1) wherein one of R2 and R3 is a hydrogen atom, the other is methyl group, R4 is a hydroxyl group, and R1 is a group represented by the aforementioned formula (vi) (Rc represents —H, and Rd represents —CH$_3$). Further, 4-methylergost-7-en-3-ol is a compound represented by the aforementioned general formula (1) wherein one of R2 and R3 is a hydrogen atom, the other is methyl group, R4 is a hydroxyl group, and R1 is a group represented by the aforementioned formula (vi) (Rc and Rd both represent —CH$_3$). Further, 4-methylstigmast-7-en-3-ol is a compound represented by the aforementioned general formula (1) wherein one of R2 and R3 is a hydrogen atom, the other is methyl group, R4 is a hydroxyl group, and R1 is a group represented by the aforementioned formula (i).

The agent, food or drink of the present invention may contain one type or two or more arbitrary types of the aforementioned compounds.

It is known that lophenol is contained in plants, and the compound of the present invention can be produced according to the known method for producing lophenol (Yamada A., "Experimental Methods of Biochemistry", Vol. 24, Experimental Methods for Fat and Lipid Metabolism, p. 174, Gakkai Shuppan Center, 1989). The compound of the present invention can be obtained by, for example, extracting the compound from a plant containing the same using a method such as extraction with an organic solvent or extraction with hot water and purifying the obtained extract. In the present invention, although the compound of the present invention may be purified, a composition such as a plant extract or a fraction thereof may also be used so long as it contains an effective amount of the compound.

The compound of the present invention or the composition containing the same can be produced in such a manner that, for example: from a plant belonging to the family Liliaceae, a part or crushed product thereof containing the compound of the present invention, a fraction containing the compound is extracted with an organic solvent or hot water and concentrated.

Examples of the aforementioned plant belonging to the family Liliaceae include plants belonging to the genus *Aloe* or *Allium*. Examples of the plants of the genus *Aloe* include *Aloe vera* (*Aloe barbadensis* Miller), *Aloe ferox* Miller, *Aloe africana* Miller, *Aloe arborescen* Miller var. *natalensis* Berger, *Aloe spicata* Baker and so forth. In the production of the compound of the present invention or a composition containing the same, although the whole of the aforementioned plant may be used, it is preferable to use mesophyll (clear gel portion) thereof. Such a plant or a part thereof is disrupted preferably by using a homogenizer or the like and thereby liquefied, and the compound of the present invention or a composition containing the same is extracted from the disruption product by using an organic solvent or hot water. Examples of the organic solvent include alcohols such as methanol, ethanol and butanol; esters such as methyl acetate, ethyl acetate, propyl acetate and butyl acetate; ketones such as acetone and methyl isobutyl ketone; ethers such as diethyl ether and petroleum ether; hydrocarbons such as hexane, cyclohexane, toluene and benzene; halogenated hydrocarbons such as carbon tetrachloride, dichloromethane and chloroform; heterocyclic compounds such as pyridine; glycols such as ethylene glycol; polyhydric alcohols such as polyethylene glycol; nitrile solvents such as acetonitrile, mixtures of these solvents and so forth. Further, these solvents may be anhydrous or hydrous. Among these solvents, ethyl acetate/butanol mixture (3:1) and chloroform/methanol mixture (2:1) are particularly preferred.

As the extraction method, a method used for usual extraction of a plant component can be used. Usually used is, for example, a method of refluxing 1 to 300 parts by mass of an organic solvent with 1 part by mass of fresh plant or dried plant with heating at a temperature below the boiling point of the solvent and stirring or shaking, or a method of performing extraction by ultrasonication at room temperature. By isolating insoluble matters from the extraction liquor using a suitable method such as filtration or centrifugation, a crude extract can be obtained.

The crude extract can be purified by various types of chromatography such as normal or reverse phase silica gel column chromatography. When a gradient of chloroform/methanol mixture is used in normal phase silica gel column chromatography as an elution solvent, the compound of the present invention is eluted with a mixing ratio of chloroform:methanol=about 25:1. Further, when a hexane/ethyl acetate mixture (4:1) is used in reverse phase silica gel column chromatography as an elution solvent, the compound of the present invention is eluted in a fraction eluted at an early stage. The obtained fraction can be further purified by HPLC or the like.

Further, the compound used for the present invention may also be produced by a chemical synthesis method or a biological or an enzymatic method using microorganisms, enzymes or the like.

Whether a compound or a composition containing the same obtained as described above is or contains the compound of the present invention can be confirmed by, for example, mass spectrometry (MS), nuclear magnetic resonance (NMR) spectroscopy or the like.

The compound of the present invention has an effect of inhibiting visceral fat accumulation, and thus can prevent the visceral fat type obesity. Therefore, the compound of the present invention can be used as an active ingredient of an agent or food or drink for inhibiting visceral fat accumulation.

Furthermore, because leaf-skin of *Aloe* vera contains barbaloin and aloe-emodin which have a laxative action, the components have been considered to be unfavorable for use in an agent or food or drink which is not expected to have the laxative action. Therefore, it is preferable that the composition containing the compound of the present invention do not contain the aforementioned components. In addition, the mesophyll of *Aloe* vera or a crushed product thereof can be used as an active ingredient of the agent for inhibiting visceral fat accumulation.

The compound of the present invention has an effect of inhibiting visceral fat accumulation, and thus can prevent the visceral fat type obesity. Therefore, the compound of the present invention per se can be used as an active ingredient of the agent for inhibiting visceral fat accumulation of the present invention and food or drink comprising the agent. Further, an organic solvent extract or a hot water extract of a plant or a fraction thereof containing the compound of the present invention (hereinafter referred to as "extract etc.") may also be used as an active ingredient of the agent or food or drink. In this case, the aforementioned extract etc. to be contained in the agent preferably contains at least 0.001% by dry mass, more preferably 0.01 to 1% by dry mass, particularly preferably 0.05 to 1% by dry mass, of the compound of the present invention. Further, the aforementioned extract etc. to be contained in the food or drink preferably contains at least 0.0001% by dry mass, more preferably 0.001 to 1% by dry mass, particularly preferably 0.005 to 1% by dry mass, of the compound of the present invention. The aforementioned extract etc. may contain two or more types of the compound of the present invention. Further, the aforementioned extract etc. may be a solution, or can also be lyophilized or spray-dried in a conventional manner and stored or used as powder.

As the agent for inhibiting visceral fat accumulation of the present invention, the compound of the present invention or a composition containing the same per se, or the compound of the present invention or a composition containing the same combined with a pharmaceutically acceptable carrier can be orally or parenterally administered to a mammal including human. In the agent for inhibiting visceral fat accumulation of the present invention, the compound of the present invention may be a pharmaceutically acceptable salt. Examples of the pharmaceutically acceptable salt include both metal salts (inorganic salts) and organic salts including, for example, those listed in "Remington's Pharmaceutical Sciences," 17th edition, p. 1418, 1985. Specific examples thereof include, but not limited to, inorganic acid salts such as hydrochloride, sulfate, phosphate, diphosphate and hydrobromate, and organic acid salts such as malate, maleate, fumarate, tartarate, succinate, citrate, acetate, lactate, methanesulfonate, p-toluenesulfonate, pamoate, salicylate and stearate. Furthermore, the salt may be a salt with a metal such as sodium, potassium, calcium, magnesium and aluminum or a salt with an amino acid such as lysine. Furthermore, solvates such as hydrates of the aforementioned compound or pharmaceutically acceptable salts thereof also fall within the scope of the present invention.

Dosage form of the agent for inhibiting visceral fat accumulation of the present invention is not particularly limited and can be suitably selected depending on the therapeutic purpose. Specific examples thereof include tablet, pill, powder, solution, suspension, emulsion, granules, capsule, syrup, suppository, injection, ointment, patch, eye drop, nasal drop and so forth. For the preparation, additives generally used in usual preventive agents for inhibiting visceral fat accumulation as pharmaceutical carriers such as excipients, binders, disintegrating agents, lubricants, stabilizers, flavoring agents, diluents, surfactants and solvents for injection and so forth can be used. Furthermore, so long as the effect of the present invention is not degraded, the compound of the present invention or the extract etc. containing the same can be used in combination with other agents having an effect of inhibiting visceral fat accumulation.

Although the amount of the compound of the present invention or the extract etc. containing the same contained in the agent for inhibiting visceral fat accumulation of the present invention is not particularly limited and can be suitably selected, the amount may be, for example, at least 0.001% by mass, preferably 0.01 to 1% by mass, particularly preferably 0.05 to 1% by mass, in terms of the amount of the compound of the present invention.

The agent for inhibiting visceral fat accumulation of the present invention has the effect of inhibiting visceral fat accumulation, and thus can prevent the visceral fat type obesity. The visceral fat type obesity generally refers to a state where an area of visceral fat is 100 $cm^2$ or more, and according to the diagnostic criteria for metabolic syndrome, refers to a case where a Japanese male has a waist size of 85 cm or more, or a Japanese female has a waist size of 90 cm or more (Internal Medicine, vol. 94, p. 188-203, 2005). In addition, the agent for inhibiting visceral fat accumulation of the present invention is preferably used for treatment of a patient who has a larger amount of the visceral fat accumulated than a healthy person.

In addition, the agent for inhibiting visceral fat accumulation of the present invention can ameliorate or prevent diseases, complications and the like caused by the visceral fat accumulation, such as abnormal lipid metabolism and cardiovascular diseases, and can also reduce risks of those diseases, complications and the like. Examples of the various diseases caused by the visceral fat accumulation include obesity, in particular, visceral fat type obesity, hyperlipidemia, diabetes, hypertension and arteriosclerosis. Examples of the complications caused by those diseases include: diabetic retinopathy, nephropathy, neuropathy, and diabetic gangrene caused by diabetes; cerebral stroke, nephrosclerosis, and renal failure caused by hypertension; and cerebral stroke, cerebral infarction, cardiovascular diseases such as angina pectoris and cardiac infarction, and nephropathy such as uremia, nephrosclerosis, and renal failure caused by arteriosclerosis disease. In addition, the inventors of the present invention have found that the compound of the present invention has an effect of ameliorating hyperglycemia by reducing a hemoglobin A1c level (WO 2005/094838). It is preferred that the diseases to which the agent for inhibiting visceral fat accumulation of the present invention is applied are not accompanied with a state where the hemoglobin A1c level is higher than that of a healthy person.

Further, the agent for inhibiting visceral fat accumulation of the present invention is useful for preventing onset of metabolic syndrome. The effect of the agent of inhibiting or reducing the accumulation of the visceral fat as described above is extremely effective for preventing the onset of metabolic syndrome and metabolic syndrome-related arteriosclerotic diseases, and lifestyle-related diseases indicated as risk factors thereof, such as diabetes, hypertension, and hyperlipidemia, and complications associated with those diseases. Furthermore, "metabolic syndrome" as used in the present invention refers to a state where arteriosclerosis is easily occurred and where there is a combination of symptoms regarded as risk factors of pathosis of the multiple risk factor syndrome, such as hyperinsulinemia, abnormal glucose tolerance or hyperglycemia, abnormal lipid metabolism, hyperlipidemia (hypertriglyceridemia and hypo-HDL-cholesterolemia), hypertension, obesity, and visceral fat accumulation.

The administration time of the agent of the present invention is not particularly limited and can be suitably selected according to the method for treating an objective disease. Furthermore, the administration route is preferably determined depending on the dosage form, age, sex and other conditions of patients, severity of symptoms of patients and so forth. The dose of the agent of the present invention is suitably selected depending on the dosing regimen, age and sex of patients, severity of disease, other conditions of patients and so forth. The amount of the compound of the present invention as an active ingredient is usually selected from the range of, preferably 0.001 to 50 mg/kg/day, more preferably 0.01 to 1 mg/kg/day, as a tentative dose. Furthermore, when an extract etc. containing the compound of the present invention is used, the dry weight of the extract etc. is selected from the range of, preferably 0.1 to 1000 mg/kg/day, more preferably 1 to 100 mg/kg/day, as a tentative amount. In any case, the dose can be ingested in a day, once or several times as divided portions.

The compound of the present invention or the composition containing the same can be added to food or drink (a drink or a food) to produce a food or drink having an effect of inhibiting visceral fat accumulation. The form and property of the food or drink are not particularly limited so long as the effect of the active ingredient is not degraded, and the food or drink can be orally ingested, and it can be produced in a conventional manner by using raw materials usually used for food or drink except that the aforementioned active ingredient is added. The amount of the compound of the present invention or the extract etc. containing the same contained in the food or drink of the present invention is not particularly limited and can be suitably selected. For example, the compound of the present invention or the extract etc. containing the same is contained in the food or drink in an amount of at least 0.0001% by mass, preferably 0.001 to 1% by mass, particularly preferably 0.005 to 1% by mass, in terms of the amount of the compound of the present invention.

The food or drink of the present invention can be applied to various uses which utilize the effect of reducing visceral fat. For example, it can be used as food or drink suitable for a person who began to worry about their waist size, food or drink suitable for a person who began to worry about blood lipid, and food or drink useful for reducing or removing risk factors of metabolic syndrome and the like.

"Inhibition of visceral fat accumulation" as used in relation to the food or drink of the present invention means that various kinds of adverse effects on health induced by the visceral fat accumulation are ameliorated or prevented. "Amelioration of visceral fat type obesity", "prevention of visceral fat type obesity", "reduction of visceral fat", "prevention of visceral fat accumulation", and the like can also be exemplified as the same meaning as the aforementioned term "inhibition of visceral fat accumulation " in the present invention.

In addition, the food or drink of the present invention is useful for ameliorating or preventing diseases caused by the visceral fat accumulation, such as abnormal lipid metabolism, cardiovascular diseases, and the like typified by hyperlipidemia. The food or drink of the present invention can also be used for preventing the onset of visceral fat type obesity and metabolic syndrome, and the like. Further, the food or drink of the present invention can treat or prevent various diseases, complications, and the like caused by the visceral fat accumulation, and can reduce the risks of those diseases, complications and the like, as mentioned above for the agent of the present invention.

The food or drink of the present invention is preferably marketed as food or drink attached with an indication that the food or drink is used for inhibiting visceral fat accumulation, for example, "food or drink containing a compound having an effect of inhibiting visceral fat accumulation indicated as 'For inhibiting visceral fat accumulation'", or "food or drink containing a plant extract indicated as 'For inhibiting visceral fat accumulation'" and the like. In addition, because the compound of the present invention or the composition or the like containing the same has the effect of inhibiting visceral fat accumulation, the indication that the food or drink is for inhibiting visceral fat accumulation may also have a meaning of ameliorating the visceral fat type obesity. Therefore, the food or drink of the present invention can also be indicated as "For ameliorating visceral fat type obesity". In other words, the aforementioned indication that food or drink is for inhibiting visceral fat accumulation may be replaced by the indication of "For ameliorating visceral fat type obesity".

The wording used for such an indication as mentioned above is not limited to the wording "For inhibiting visceral fat accumulation" or "For ameliorating visceral fat type obesity", and there is no need to say that other wordings are encompassed within the scope of the present invention so long as the wordings indicate the effect of inhibiting the visceral fat accumulation, or preventing or ameliorating the visceral fat type obesity. As such a wording, for example, an indication based on various uses allowing consumers to recognize the effect of inhibiting visceral fat accumulation or ameliorating the visceral fat type obesity is also possible. Examples of the indication include "suitable for a person who began to worry about waist size", "suitable for a person who tend to be visceral fat type obesity", and "useful for reducing or removing risk factors (risks) of metabolic syndrome".

The aforementioned term "indication" includes all actions for informing consumers the aforementioned use, and any indications reminding or analogizing the aforementioned use fall within the scope of the "indication" of the present invention regardless of purpose, content, objective article, medium etc. of the indication. However, the indication is preferably made with an expression that allows consumers to directly recognize the aforementioned use. Specific examples include actions of indicating the aforementioned use on goods or packages of goods relating to the food or drink of the present invention, actions of assigning, delivering, displaying for the purpose of assigning or delivering or importing such goods or packages of goods indicated with the aforementioned use, displaying or distributing advertisements, price lists or business papers relating the goods with indicating the aforementioned use, or providing information including those as contents with indicating the aforementioned use by an electromagnetic method (Internet etc.) and so forth. On the other hand, the indication is preferably an indication approved by the administration etc. (for example, an indication in a form based on an approval, which is qualified on the basis of any of various legal systems provided by the administration), and it is particularly preferably an indication on advertisement materials at the sales spots such as packages, containers, catalogs, pamphlets and POPs, others documents and so forth.

Examples of the indication further include indications as health food, functional food, enteric nutritive food, food for special dietary uses, food with nutrient function claims, quasi-drug and so forth as well as indications approved by the Ministry of Health, Labor and Welfare, for example, indications approved on the basis of the system of food for specified health uses and similar systems. Examples of the latter include indications as food for specified health uses, indications as food for specified health uses with qualified health claims, indications of influence on body structures and functions, indications of reduction of disease risk claims and so forth, and more precisely, typical examples include indications as food for specified health uses (especially indications of use for health) provided in the enforcement regulations of Health Promotion Law (Japan Ministry of Health, Labor and Welfare, Ministerial ordinance No. 86, Apr. 30, 2003) and similar indications.

The present invention will be explained more specifically with reference to the following examples. However, the scope of the present invention is not limited to the following examples.

First, Preparation Example describes that the compound of the present invention or composition can be produced from a plant belonging to a Liliaceae.

Preparation Example 1

In an amount of 100 kg of mesophyll (clear gel portion) of *Aloe* vera was liquefied by using a homogenizer, added with 100 L of an ethyl acetate/butanol mixture (3:1) and stirred.

The mixture was left standing overnight, and then the ethyl acetate/butanol mixture and the aqueous layer were separated to recover the ethyl acetate/butanol mixture. The extract from this ethyl acetate/butanol mixture obtained by concentrating the ethyl acetate/butanol mixture under reduced pressure weighed 13.5 g. A solution of 13 g of this extract dissolved in 1 mL of a chloroform/methanol mixture (1:1) was loaded on a column filled with 400 g of Silica Gel 60 (Merck Ltd.) to attain adsorption of the components to the column, then the components were eluted with a chloroform/methanol mixture by the stepwise gradient method, in which the methanol concentration was increased stepwise (mixing ratios of chloroform:methanol=100:1, 25:1, 10:1, 5:1 and 1:1), and the eluate was fractionated for each mixing ratio of the aforementioned mixture. It was confirmed by normal phase and reverse phase thin layer chromatography (Merck Ltd., Silica Gel 60F254 and RP-18F2543) that, among these fractions, the compound of the present invention existed in the fraction eluted with the mixture of chloroform:methanol=25:1.

This crude purified substance (crude purification product 1) containing the compound of the present invention weighed 3 g. Further, the yields of the crude purification products obtained in the above operation from the fractions eluted with the mixtures of chloroform:methanol=10:1 and 1:1 were 1.17 and 2.27 g, respectively. The solvents of these fractions were removed, then each extract was dissolved in 1 mL of a chloroform/methanol mixture (1:1) and loaded on a column filled with 100 g of Silica Gel 60 to attain adsorption of the components to the column, and then the components were eluted with 1100 mL of a hexane/ethyl acetate mixture (4:1). The eluted fractions were collected as aliquots of 300 mL (fraction A), 300 mL (fraction B) and 500 mL (fraction C) in this order. The yields obtained after removing the solvents from the fractions A, B and C were 0.6 g, 1.35 g and 0.15 g, respectively. It was confirmed by normal phase and reverse phase thin layer chromatography that the compound of the present invention had been concentrated in the fraction A (crude purification product 2). This crude purification product 2 was further separated by HPLC using COSMOSIL C18 (Nacalai Tesque, Inc.) with a chloroform/hexane mixture (85:15) to obtain 1.3 mg of compound 3 (4-methylcholest-7-en-3-ol), 1.2 mg of compound 4 (4-methylergost-7-en-3-ol) and 1 mg of compound 5 (4-methylstigmast-7-en-3-ol). The structures of these compounds were confirmed by MS and NMR.

Example 1

In Example 1, an inhibitory effect of a compound having a lophenol skeleton on visceral fat accumulation was investigated by using ZDF (Zucker Diabetic Fatty) rats that are model animals for obese diabetes.

(1) Preparation of Samples

Compound 3 (4-methylcholest-7-en-3-ol), Compound 4 (4-methylergost-7-en-3-ol), and Compound 5 (4-methylstigmast-7-en-3-ol) which were produced in Preparation Example 1 were used as Test Samples 1, 2, and 3, respectively. Each of the test samples was dissolved in DMSO, and a concentration of each of the compounds in each of the test samples was adjusted with distilled water to be 10 µg/ml, thereby preparing Test Samples 1-1, 2-1, and 3-1. Test Samples 1-2, 2-2, and 3-2 each having the concentration of a compound of 1 µg/ml were prepared. In addition, final concentration of DMSO was adjusted to 0.2%. Further, a solution without the test samples was prepared as a negative sample.

(2) Test Method 6-week-old male ZDF rats (purchased from Charles River Laboratories, Inc., US) were preliminarily fed with a high fat diet (Research Diet Inc.) for 1 month, and the rats were then divided into groups of 6 rats each. The groups of rats were orally administered with 1 ml of solutions of the negative sample, Test Samples 1-1, 1-2, 2-1, 2-2, 3-1, and 3-2, respectively, per 400 g of body weight of a rat once a day successively for 44 days by using a sonde. At 45th day from initiation of the administration, mesenteric fat weights were measured as the visceral fat.

(3) Test Results

Table 1 shows the mesenteric fat weights at the 45th day from the initiation of the administration. The group of rats administered with the negative sample had a mesenteric fat weight of 6.83±1.10 g, and the groups administered with Test Samples 1-1, 2-1, and 3-1 each having a compound concentration of 10 µg/ml, respectively, had the mesenteric fat weights of 4.48±1.34 g, 3.78±0.26 g, and 3.36±1.67 g, the fat weights being 65.0%, 54.9%, and 48.7% of that of the group administered with the negative sample. Therefore, it was confirmed that Test Samples 1-1, 2-1, and 3-1 had significant effects of inhibiting visceral fat accumulation. On the other hand, the administration of Test Samples 1-2, 2-2, and 3-2 each having a compound concentration of 1 µg/ml, respectively, resulted in tendency to reduce the visceral fat, but no significant effect was observed. Furthermore, there was no side effects observed from pathologic viewpoints. In addition, p values in Table 1 indicate significance probability by Tukey-Kramer's test.

TABLE 1

| Sample (concentration of active ingredient) | | Mesenteric fat weight (g) | p value |
|---|---|---|---|
| Test Sample 1-1 | (10 µg/ml) | 4.48 ± 1.34* | 0.0380 |
| Test Sample 1-2 | (1 µg/ml) | 5.63 ± 1.25 | 0.3150 |
| Test Sample 2-1 | (10 µg/ml) | 3.78 ± 0.26* | 0.00004 |

TABLE 1-continued

| Sample (concentration of active ingredient) | | Mesenteric fat weight (g) | p value |
|---|---|---|---|
| Test Sample 2-2 | (1 µg/ml) | 5.74 ± 1.57 | 0.3332 |
| Test Sample 3-1 | (10 µg/ml) | 3.36 ± 1.67* | 0.0002 |
| Test Sample 3-2 | (1 µg/ml) | 6.10 ± 1.67 | 0.5019 |
| Negative sample | | 6.89 ± 0.61 | — |

In the Table, "*" indicates that there was a statistically significant effect of inhibiting visceral fat accumulation.

Example 2

In Example 2, an effect of the compound having lophenol skeleton on an amount of food ingestion (amount of food consumption) and an increase in body weight (amount of increased body weight) of rats was investigated.

(1) Preparation of Samples

Test Samples 1-1, 2-1, and 3-1 which were used in Example 1 were used as test samples. In addition, a solution without the test samples was prepared as a negative sample.

(2) Test Method 6-week-old male ZDF rats (purchased from Charles River Laboratories, Inc., US) were preliminarily fed with a high fat diet (Research Diet Inc.) for 1 month, and body weights of the rats were measured and the rats were then divided into groups of 6 rats each. The groups of rats were orally administered with 1 ml of solutions of Test Samples 1-1, 2-1, and, 3-1 and the negative sample, respectively, per 400 g of body weight of a rat once a day successively for 44 days by using a sonde. 42 days after initiation of the administration, the body weights of the rats were measured, and differences between the body weights on the 42nd day and those measured before the initiation of the administration were regarded as amounts of increased body weights. In addition, weights of food consumed per day were measured about once a week from the day of the initiation of the administration, and an average of the weights was regarded as an amount of food consumption per day.

(3) Test Results

Table 2 shows the amounts of food consumption per day and amounts of increased body weight during 42 days per rat. It was observed that the groups administered with Test Samples 1-1, 2-1, and 3-1, respectively, did not show significant increase or decrease in amount of food consumption as compared with the group administered with the negative sample. In addition, the amounts of increased body weight (increases in body weight) of the groups administered with Test Samples 1-1, 2-1, and 3-1, respectively, were almost the same as that of the group administered with the negative sample. Thus, it was found that the compound having a lophenol skeleton does not affect the amount of food ingestion and increase in body weight of rats.

TABLE 2

| Sample | Amount of food consumption (g) | Increased body weight (g) |
|---|---|---|
| Test Sample 1-1 | 21.7 ± 2.0 | 137.7 ± 10.8 |
| Test Sample 2-1 | 21.7 ± 2.2 | 128.7 ± 14.5 |
| Test Sample 3-1 | 21.4 ± 1.3 | 152.7 ± 28.1 |
| Negative sample | 22.5 ± 1.2 | 140.7 ± 18.8 |

Industrial Applicability

According to the present invention, there can be provided an agent for inhibiting visceral fat accumulation, which is capable of maintaining a standard body weight without decreasing the body weight, and is effective for inhibiting progression of obesity without excessive diet restriction or the like, and a physiologically functional food or drink such as food for specified health uses containing the agent for inhibiting visceral fat accumulation. Thus, diseases, complications, and the like caused by the visceral fat accumulation, such as abnormal lipid metabolism and cardiovascular diseases can be ameliorated or prevented, and risks of those diseases, complications, and the like can also be reduced. In addition, the present invention also provides an effect of preventing onset of metabolic syndrome and lifestyle-related diseases which are indicated as risk factors of metabolic syndrome, such as diabetes, hypertension, and hyperlipidemia.

What is claimed is:

1. A method of inhibiting visceral fat accumulation, to a patient where visceral fat accumulation is to be inhibited, which comprises administering an ethyl acetate/butanol mixture extraxt or a chloroform/methanol mixture extract of a plant of the genus Aloe, or a fraction thereof, which comprises at least 0.001% by dry mass of a compound selected from the group consisting of 4-methylcholest-7-en-3-ol, 4-methylergost-7-en-3-ol, and 4-methylstigmast-7-en-3-ol.

2. The method according to claim 1, wherein the mixture is ethyl acetate/butanol (3:1)

3. The method according to claim 1, wherein the mixture is chloroform/methanol (2:1)

* * * * *